(12) United States Patent
Butterly et al.

(10) Patent No.: US 6,414,142 B1
(45) Date of Patent: Jul. 2, 2002

(54) PROCESS FOR PREPARING POTASSIUM CLAVULANATE

(75) Inventors: Paul Gerard Butterly, Clark; Gilroy John Keohane, Piscataway; Esin Fatma Kosal, Holmdel, all of NJ (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 08/973,936

(22) PCT Filed: Jun. 12, 1997

(86) PCT No.: PCT/US97/10317

§ 371 (c)(1),
(2), (4) Date: Dec. 8, 1997

(87) PCT Pub. No.: WO97/47301

PCT Pub. Date: Dec. 18, 1997

Related U.S. Application Data

(60) Provisional application No. 60/020,480, filed on Jun. 13, 1996.

(51) Int. Cl.[7] .............................................. C07D 503/18
(52) U.S. Cl. ...................................................... 540/349
(58) Field of Search .......................................... 540/349

(56) References Cited

U.S. PATENT DOCUMENTS

| | | | | |
|---|---|---|---|---|
| 4,454,069 A | * | 6/1984 | Cook et al. | 540/347 |
| 4,647,659 A | | 3/1987 | Cook et al. | 540/349 |
| 5,288,861 A | * | 2/1994 | Clark et al. | 540/347 |
| 5,441,945 A | | 8/1995 | Yoshikawa | 514/80 |
| 5,726,170 A | * | 3/1998 | Callewaer | 514/210 |
| 5,821,364 A | * | 10/1998 | Weber | 540/349 |
| 5,859,238 A | * | 1/1999 | Copar | 50/349 |
| 5,985,625 A | * | 11/1999 | Capuder | 540/239 |

FOREIGN PATENT DOCUMENTS

| | | |
|---|---|---|
| EP | 0 277 008 A1 | 8/1988 |
| GB | 1508977 * | 4/1978 |
| GB | 1543563 * | 4/1979 |
| WO | WO 93/25557 | 12/1993 |
| WO | WO 94/21647 | 9/1994 |
| WO | WO 95/21173 | 8/1995 |
| WO | WO 97/05142 | 2/1997 |

OTHER PUBLICATIONS

Eggers, D.F. Jr et al, "Physical Chemistry", 1964, John Wiley, New York, pp. 519–522.*
Pauling, Linus, "General Chemistry, 2nd Ed.", 1953, Freeman, San Francisco, p141–142.*

* cited by examiner

Primary Examiner—Mukund J. Shah
Assistant Examiner—Thomas C McKenzie
(74) Attorney, Agent, or Firm—Janice E. Williams; Charles M. Kinzig

(57) ABSTRACT

A new crystalline form of potassium clavulanate is disclosed. Also disclosed are a process for producing the new crystalline form of potassium clavulanate, pharmaceutical compositions containing it and methods of treating bacterial infections.

4 Claims, 4 Drawing Sheets

PROCESS FOR PREPARING POTASSIUM CLAVULANATE

This application is 35 U.S.C. §371 National Stage application of PCT/US97/10317, filed Jun. 13, 1997, which claims priority from U.S. Provisional Application No. 60/020,480, filed Jun. 13, 1996.

FIELD OF THE INVENTION

This invention relates to an improved process for preparing potassium clavulanate, a novel crystalline form of potassium clavulanate and the use thereof in treating bacterial infections.

BACKGROUND OF THE INVENTION

Clavulanic acid and its salts are disclosed in British Patent No. 1508977 as β-lactamase inhibitors capable of enhancing the antibacterial effectiveness of β-lactam antibiotics such as penicillins and cephalosporins against many β-lactamase producing bacteria. Antibacterial compositions comprising potassium clavulanate and amoxycillin are commercially available under the trade name 'Augmentin' (registered Trademark of SmithKline Beecham Corporation), and certain oral dry unit-dose antibacterial compositions of potassium clavulanate and amoxycillin are described in British Patent No. 2005538. Antibacterial compositions comprising potassium clavulanate and ticarcillin are commercially available under the trade name 'Timentin' (registered Trademark of SmithKline Beecham Corporation). Potassium clavulanate may also be formulated with other penicillins and cephalosporins to enhance their antibacterial efficacy, and also may be formulated alone for separate co-administration with penicillins and cephalosporins.

British Patent No. 1508977 also discloses that salts of clavulanic acid can be obtained by absorbing the clavulanate anion in filtered broth onto an anion exchange resin, eluting therefrom with an electrolyte, desalting the resulting solution, applying the desalted solution to a further anion exchange resin, chromatographically eluting therefrom with an electrolyte, desalting the resulting solution and thereafter removing the solvent. This process can be used to give acceptable yields of pure material, but the use of resin columns involves significant investment and they can introduce limitations in large scale production operations.

British Patent No. 1543563 discloses a process for the preparation of clavulanic acid salts via precipitation by lithium carbonate.

In European Patent No. 0026044, the use of the tertiary-butylamine salt of clavulanic acid as an intermediate in the preparation of clavulanic acid and pharmaceutically acceptable salts and esters thereof as well as a process for the preparation of clavulanic acid or a pharmaceutically acceptable salt or ester thereof comprising converting the tertiary-butylamine salt of clavulanic acid into clavulanic acid or a pharmaceutically acceptable salt or ester thereof are described. The tertiary-butylamine salt of clavulanic acid, which can be obtained in high purity, has been disclosed in Belgian Patent No. 862211, but only as a suitable ingredient for pharmaceutical formulations. European Patent No. 0026044 further discloses a process for the purification of clavulanic acid or a pharmaceutically acceptable salt or ester thereof which comprises contacting impure clavulanic acid in an organic solvent with tertiary-butylamine, isolating the tertiary-butylamine salt of clavulanic acid, and converting the thus formed tertiary-butylamine salt into calvulanic acid or a pharmaceutically acceptable salt or ester thereof.

Crystalline potassium clavulanate generally exists in the form of rod-like or needle-like crystals, which are generally relatively large, long crystals, sometimes agglomerated into plate-like crystals, and sometimes randomly aggregated into loosely formed bundles. This form of potassium clavulanate can give rise to processing difficulties in that the material does not always flow readily, is of low bulk density, and can be difficult to sieve. U.S. Pat. No. 5,288,861 describes crystalline potassium clavulanate in the form of crystalline rosettes, each comprising a plurality of needle crystals radiating out from a common nucleation point. Such rosette form of crystalline potassium clavulanate has improved flow characteristics and sieving characteristics as compared with the standard needle form potassium clavulanate, thus resulting in advantageous pharmaceutical processing and formulation. Crystalline potassium clavulanate may also exist in a more open rosette, or starburst, form as described in U.S. Pat. No. 5,288,861.

SUMMARY OF THE INVENTION

This invention relates to an improved process for the preparation of potassium clavulanate of the formula (I):

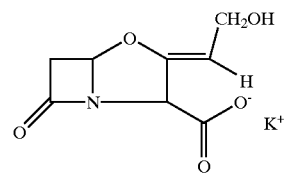

directly from the tertiary-butylamine salt of clavulanic acid which results in greater overall yield and better final product quality than the prior art processes.

The present invention also relates to a new rosette-like starburst crystalline form of potassium clavulanate.

DETAILED DESCRIPTION OF THE INVENTION

Figure 1:
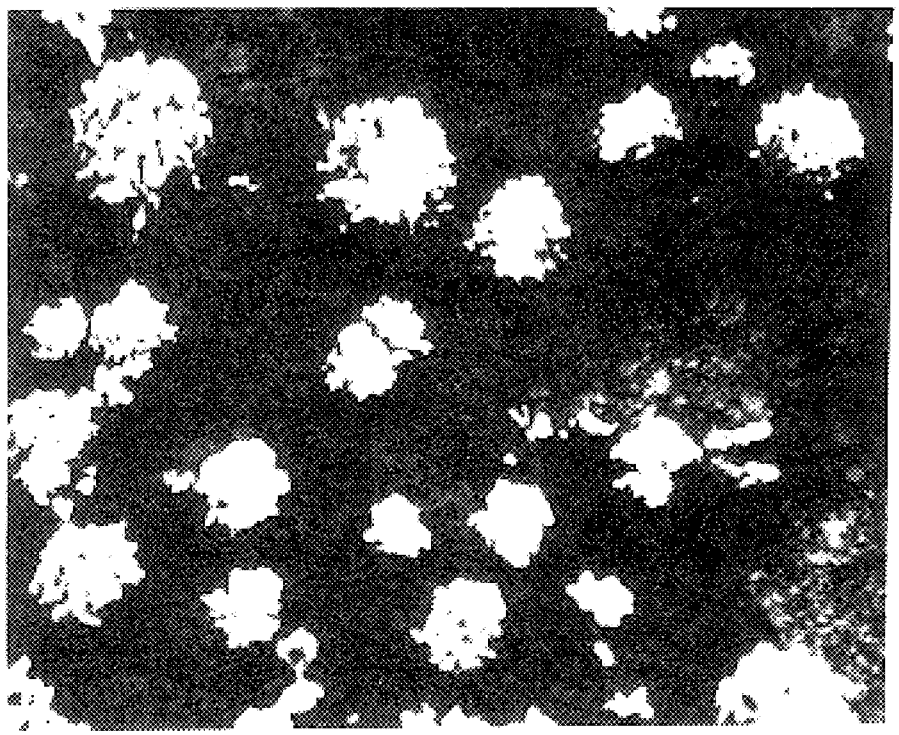
FIG. 1 shows a microphotograph of the rosette-like starburst crystalline form of potassium clavulanate at a magnification of 100×.
Figure 2:
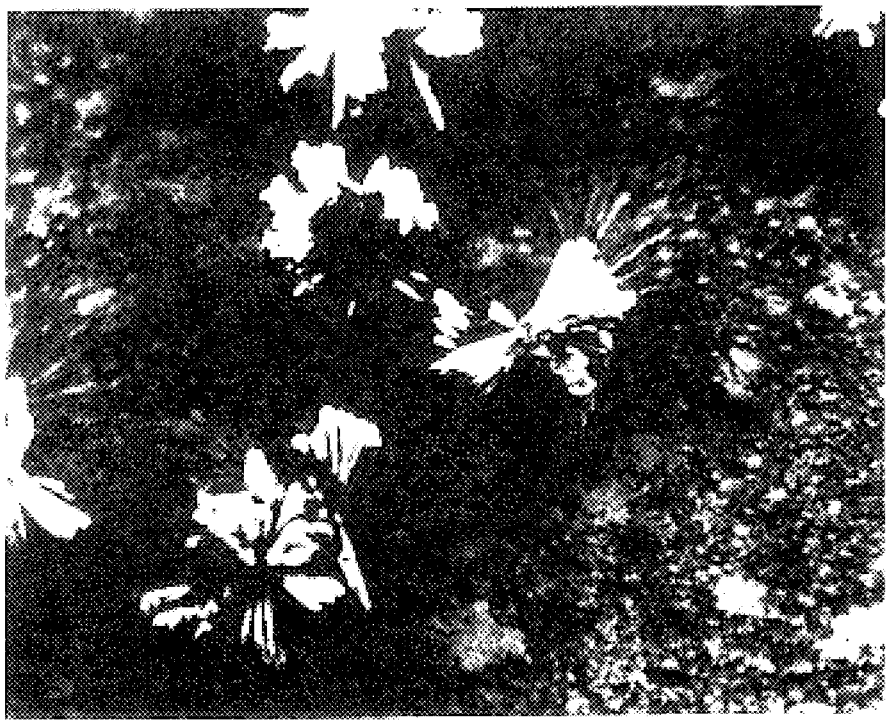
FIG. 2 shows a microphotograph of the rosette-like starburst crystalline form of potassium clavulanate at a magnification of 250×.
Figure 3:
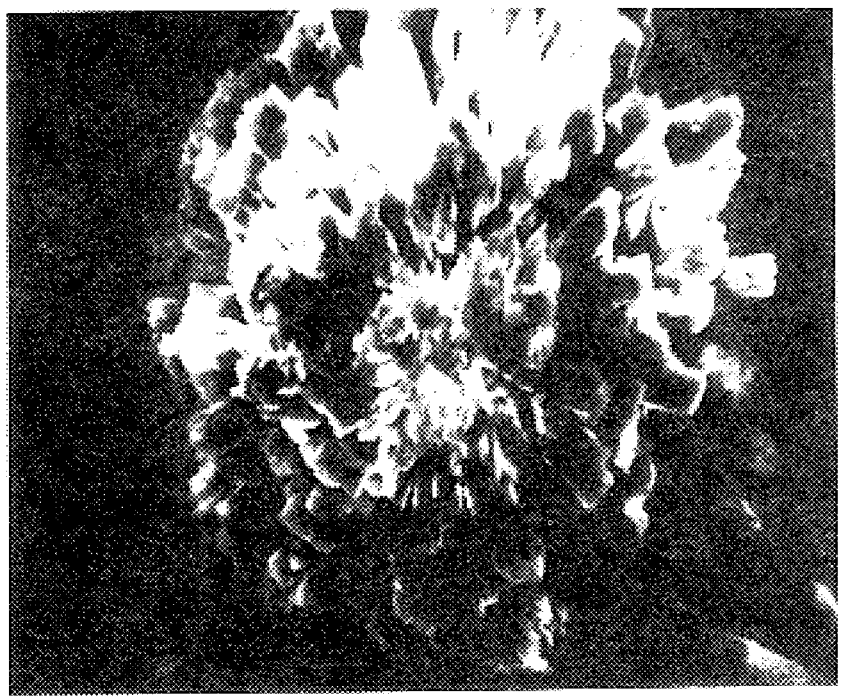
FIG. 3 shows a microphotograph of the rosette-like starburst crystalline form of potassium clavulanate at a magnification of 640×.

The present invention provides an improved process for preparing potassium clavulanate directly from the tertiary-butylamine salt of clavulanic acid. In particular, the present invention provides an improved process for preparing sterile potassium clavulanate directly from the tertiary-butylamine salt of clavulanic acid.

More specifically, the improved process of this invention comprises the reaction of the tertiary-butylamine salt of clavulanic acid (U.S. Pat. No. 4,454,069) in aqueous isopropanol with potassium 2-ethyl hexanoate in isopropanol, both solutions being sterilely filtered prior to crystallization, to produce sterile potassium clavulanate. Alternatively, if the potassium clavulanate is produced in non-sterile form, it can then be converted to sterile potassium clavulanate by standard methods known to the art, such as by carbon treatment of the non-sterile material followed by sterile filtration.

By utilizing the improved process of this invention, an entire recrystallization step of the prior art process (conversion of non-sterile potassium clavulanate to sterile potassium clavulanate) is eliminated, thus resulting in at least a 10% cost savings. The new process disclosed herein also results in an approximately 7% yield increase overall, reduction in overall cycle time, at least comparable final product quality, less solvent use, safer material transfer and in-process material handling, and better process control and reproducibility.

By carrying out the process of this invention, a new crystalline form of potassium clavulanate, which assures safer product handling and material transfer than the prior art forms, is produced. This new crystalline form of potassium clavulanate is a rosette-like starburst, different from the crystalline rosette or starburst forms described in the prior art. The new rosette-like starburst crystalline form of potassium clavulanate optimizes the advantages and minimizes the disadvantages of the prior art needle (or rod), starburst and rosette forms of potassium clavulanate.

More specifically, the new rosette-like starburst crystalline form of potassium clavulanate is less packed and generally looser than the densely packed rosette crystalline form of the prior art. Thus, the rosette-like starburst form is less likely to trap contaminants during the crystallization process and is easier to wash and purify, thereby resulting in a more highly and easily purified product. As compared to the rosette, needle and starburst crystalline forms of potassium clavulanate, the new rosette-like starburst form has a generally lower polymer level which results in greater stability and longer shelf-life. As compared to the needle and starburst crystalline forms of potassium clavulanate, the new rosette-like starburst form is less fragile and less likely to shatter. As compared to the rosette crystalline form of potassium clavulanate, the new crystalline form, although somewhat less durable, is more stable. In addition, the new crystalline form exhibits enhanced blendability as compared especially with the needle and starburst forms of crystalline potassium clavulanate. The particle size distribution for the new rosette-like starburst crystalline form of potassium clavulanate is from about 45 microns to about 98 microns which, as shown in Example 5, is significantly different from that of the prior art crystalline forms.

Figure 4:
FIG. 4 shows a microphotograph of the rosette-like starburst crystalline form of potassium clavulanate at a magnification of 1010×.
Figure 5:
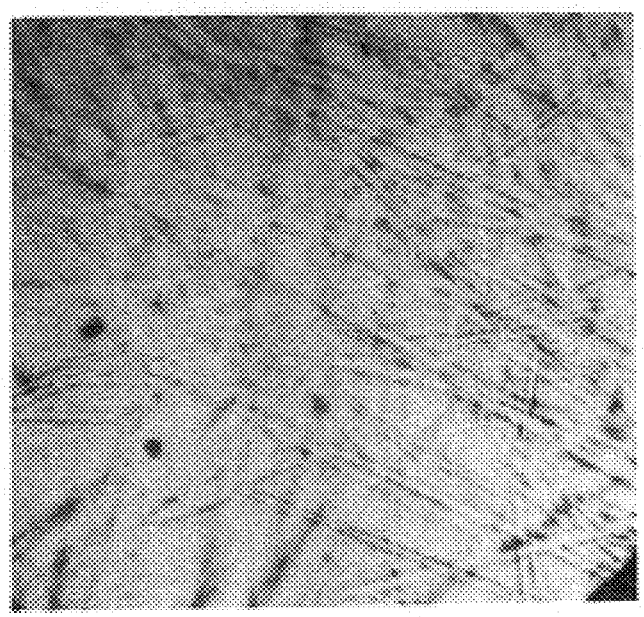
FIG. 5 shows a microphotograph of the conventional crystalline form of potassium clavulanate in large individual needles at a magnification of 400×, which are in some cases randomly formed into loosely bound aggregates.
Figure 6:
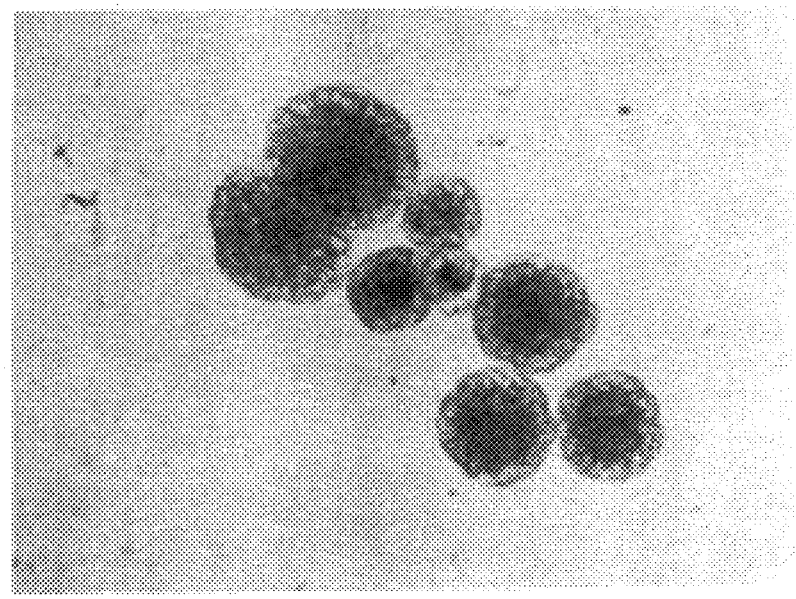
FIG. 6 shows a microphotograph of the rosette crystalline form of potassium clavulanate at a magnification of approximately 100×.
Figure 7:
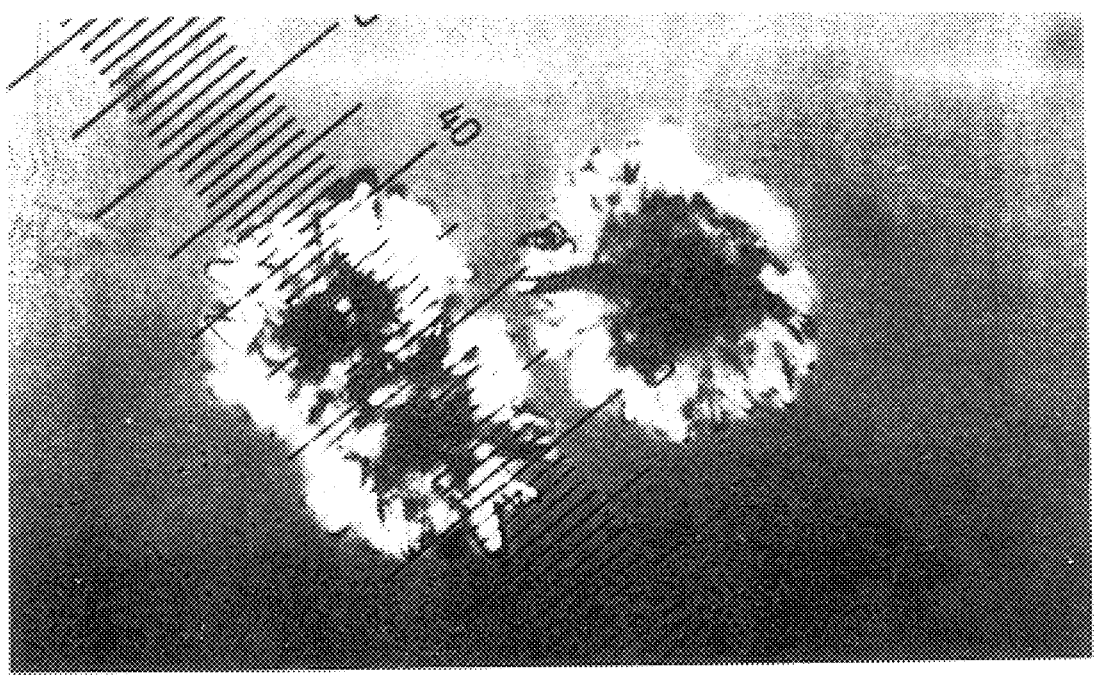
FIG. 7 shows a microphotograph of the rosette cyrstalline form of potassium clavulanate.

FIGS. 1–4 show scanning electron microscope (SEM) photographs of various samples of the new rosette-like starburst crystalline form of potassium clavulanate at magnifications of 100× (FIG. 1), 250× (FIG. 2), 640× (FIG. 3) and 1010× (FIG. 4). FIG. 5 shows, for comparison purposes, a microphotograph of a sample of the conventional crystalline form of potassium clavulanate in large individual needles at a magnification of 400×. FIGS. 6 and 7 show, for comparison purposes, the rosette form of crystalline potassium clavulanate.

The rosette-like starburst form of crystalline potassium clavulanate of the present invention may be dried, processed and formulated in a manner conventional for potassium clavulanate, but with the particular advantages of the new crystalline form described above. Optionally, the new crystalline form of potassium clavulanate of this invention can be blended with salts of other active ingredients to produce combination products.

Thus, the present invention also provides a pharmaceutical composition comprising the rosette-like starburst form of crystalline potassium clavulanate described above in admixture or conjunction with a pharmaceutically acceptable carrier o r excipient.

The present invention also provides a pharmaceutical composition comprising the rosette-like starburst form of crystalline potassium clavulanate described above in admixture or conjunction with an antibacterially active β-lactam compound, especially a penicillin or cephalosporin. Particularly preferred β-lactam compounds are amoxycillin and ticarcillin and pharmaceutically acceptable salts an d in vivo hydrolysable esters thereof.

A pharmaceutical composition according to the present invention may be adapted for oral or parenteral use, and may be used for the treatment of bacterial infections in mammals, including humans.

A pharmaceutical composition according to the present invention may, for example, be in the form of tablets, capsules, granules, suppositories, suspensions or reconstitutable powders (for subsequent dissolution to form solutions for injection or infusion). Injectable or infusable compositions, for example reconstitutable powders, of clavulanic acid and its salts are particularly important as they can give high tissue levels of the compound after administration by injection or infusion. Thus, one preferred composition of the present invention comprises the new rosette-like starburst form of crystalline potassium clavulanate in sterile form, optionally in admixture or conjunction with an antibacterially active β-lactam compound in sterile form. Such compositions may, for example, be stored in sterile vials until use. In accordance with conventional practice, such reconstitutable powders may be dissolved in a sterile pyrogen-free liquid such as water for injection B.P.

The pharmaceutical compositions according to the present invention, whether for oral or parenteral use, may be in unit dosage form. For example, a unit dose of a reconstitutable powder may be contained within a sterile vial for subsequent dissolution to give a single injectable dose.

Further details of formulating potassium clavulanate into pharmaceutical compositions, as well as details of dosages, and details of other antibacterially active β-lactam compounds for co-use with potassium clavulanate are given in British Patent No. 1508977. Such details are also applicable to the rosette-like starburst crystalline form of potassium clavulanate of the present invention.

According to further aspects, the present invention provides the use of the rosette-like starburst crystalline form of potassium clavulanate for the treatment of bacterial infections, the use of the rosette-like starburst crystalline form of potassium clavulanate in admixture or conjunction with an antibacterially active β-lactam compound for the treatment of bacterial infections, and the use of the rosette-like starburst crystalline form of potassium clavulanate in the preparation of a medicament for the treatment of bacterial infections, the medicament preferably being suitable for administration by injection or infusion.

The present invention also provides a method for the treatment of a bacterial infection in a human or animal patient which comprises co-administering thereto an antibacterially effective amount of the rosette-like starburst crystalline form of potassium clavulanate and an antibacterially active β-lactam compound, and a method for the treatment of a bacterial infection in a human or animal patient which comprises administering thereto an antibacterially effective amount of an antibacterially active β-lactam compound and a β-lactamase inhibitory amount of the rosette-like starburst crystalline form of potassium clavulanate.

Yet another aspect of this invention is the rosette-like starburst crystalline form of potassium clavulanate admixed or dry blended with amoxycillin or ticarcillin or a suitable salt thereof, in the form of a sterile reconsititutable powder, in a vial. Suitable ratios by weight of the new crystalline form of potassium clavulanate to amoxycillin and ticarcillin, all in free acid form, are from 1:1 to 1:12, preferably 1:4 to 1:8, for amoxycillin and from 1:5 to 1:30 for ticarcillin.

The Figures and Examples illustrate the present invention.

EXAMPLE 1

Preparation of 2N Potassium 2-Ethyl Hexanoate/Isopropanol Solution

Isopropanol (4 liters) and 2-ethyl hexanoic acid (1200 grams) are mixed and potassium hydroxide pellets (562 grams) are added into the mixture over 5 minutes at room temperature while stirring. The mixture is stirred for 1 hour until all the potassium hydroxide pellets are dissolved. The final solution is distilled azeotropically with 14 liters of isopropanol at 50° C. under reduced pressure (house vacuum). Then the volume is adjusted to 4 liters and filtered through filter aid. The solution is checked and adjusted for a maximum of 1% water content.

The solution (10 ml) is diluted with methanol (20 ml) and phenolphthalein is dropped into it. If a violet color formation indicates the existence of excess potassium hydroxide, the excess is determined by titrating with 0. 1N hydrochloric acid until the color disappears.

If there is no excess potassium hydroxide, the solution is titrated with 0.1 N sodium hydroxide to determine the excess 2-ethyl hexanoic acid. If the 2-ethyl hexanoic acid level is greater than 3.0%, the excess is neutralized by adding an estimated amount of 45% potassium hydroxide in water solution.

EXAMPLE 2

Preparation of tertiary-Butylamino Clavulanate Solution ("Solution 1")

Isopropanol (75 ml) and water (9 ml) are mixed and tertiary-butylamino clavulanate (20 grams) is added to the mixture. The resulting mixture is stirred for 5–10 minutes at room temperature, with warming to keep the temperature constant since the dissolution process is endothermic. Then charcoal (4.5 grams of Norit SG/Norit SX2) is added to the solution. The mixture is stirred at moderate speed for 20 minutes at room temperature. The mixture is then filtered through filter aid prepared previously by caking the filter aid on the bottom of the filter. The solution ("Solution 1") is transferred into a reservoir.

EXAMPLE 3

Preparation of 2-Ethyl Hexanoate Solution ("Solution 2")

A 2N solution (49 ml) of potassium 2-ethyl hexanoate/isopropanol is diluted with isopropanol (100 ml) then mixed thoroughly and transferred into a reservoir ("Solution 2").

EXAMPLE 4

Preparation of Crystalline Potassium Clavulanate from tertiary-Butylamino Clavulanate Isopropanol (300 ml) and acetone (75 ml) are transferred into a crystallization flask. The solvent mixture is cooled down to 15–17° C. Solution 1 and Solution 2 are concurrently added into the crystallization solution over a period of 0–3 minutes at a 2–4 ml/min addition rate.

The glassware used to prepare tertiary-butylamino clavulanate solution and the filter aid cake are washed with first 10% water in isopropanol solvent mixture (25 ml) and then with pure isopropanol (25 ml). After Solution 1 and Solution 2 are completely added into the crystallization solution, each washing is added to the crystallization solution separately at the same addition rate. Completion time of adding the two solutions is about 75 minutes.

Nucleation begins in about 10–15 minutes from start of the addition. As soon as the addition is completed, the slurry is cooled down to 0–50C and stirred moderately for 0.5 hour. The crystals are filtered and washed with acetone (100 ml) and air dried at room temperature for 2 hours.

EXAMPLE 5

Comparison of Rosette-like Starburst Potassium Clavulanate Crystals with Known Crystalline Forms of Potassium Clavulanate

| | Needles/rods | Starbursts/Broken Starbursts | Rosette-like Starbursts | Rosettes |
| --- | --- | --- | --- | --- |
| Tapped Bulk Density Range (g/ml) | 0.150–0.159 | 0.276–0.508 | 0.476–0.715 | 0.629–0.753 |
| Flowabiiity | 3.4 | N/A | 4.8 | 6.1 |
| Particle Size Distribution (microns) | 34.1–67.3 | 33.5–70.5 | 35.1–97.9 | 34.8–66.4 |

What is claimed is:

1. A process for preparing potassium clavulanate in the form of crystalline rosette-like starbursts which comprises concurrently adding a solution of potassium 2-ethyl hexanoate in isopropanol and a solution of tertiary-butylamino clavulanate in aqueous isopropanol to a mixture of isopropanol and acetone and precipitating the crystalline potassium clavulanate therefrom, and optionally isolating the crystals by filtration.

2. A process according to claim 1 in which the potassium 2-ethyl hexanoate and tertiary-butylamino clavulanate solutions are added at the same addition rate.

3. A process according to claim 1 in which the precipitation is carried out at a temperature of from about 0° C. to about 20° C.

4. A process according to claim 4 in which the precipitation is carried out at a temperature of from about 15° to about 17° C.

\* \* \* \* \*

UNITED STATES PATENT AND TRADEMARK OFFICE
CERTIFICATE OF CORRECTION

PATENT NO. : 6,414,142 B1
DATED : July 2, 2002
INVENTOR(S) : Paul Gerard Butterly, Gilroy John Keohane and Esin Fatma Kosal It is certified that error appears in the above-identified patent and that said Letters Patent is hereby corrected as shown below:

<u>Title page,</u>
Item [22], "Jun. 12, 1997" should read -- Jun. 13, 1997 --.

Signed and Sealed this

Twenty-second Day of April, 2003

JAMES E. ROGAN
*Director of the United States Patent and Trademark Office*